US005824506A

United States Patent [19]

Chan et al.

[11] Patent Number: 5,824,506

[45] Date of Patent: Oct. 20, 1998

[54] DENGUE VIRUS PEPTIDES AND METHODS

[75] Inventors: Lily Chan; Ming Guan, both of Singapore, Singapore

[73] Assignee: Genelabs Diagnostics PTE. Ltd., Singapore

[21] Appl. No.: 290,268

[22] Filed: Aug. 15, 1994

[51] Int. Cl.$^6$ .............................. G01N 33/53; C12P 21/00

[52] U.S. Cl. .............................. 435/69.3; 435/5; 435/7.1; 435/7.92; 435/7.94; 435/172.3; 435/965; 435/975; 424/186.1; 424/204.1; 424/218.1; 530/324; 530/328

[58] Field of Search .............................. 424/186.1, 204.1, 424/218.1; 435/5, 69.3, 172.3, 7.1, 7.92, 7.94, 965, 975; 530/350, 324, 328

[56] References Cited

FOREIGN PATENT DOCUMENTS

WO/88/03032 5/1988 WIPO .

OTHER PUBLICATIONS

Blok et al., Arch. Virol. (1991) 118:209–223.

Blok et al., Virology, 187, 573–590 (1992).

Irie et al., Gene, 75 (1989) 197–211.

Aaskov, J.G., et al. "Serologically defined linear epitopes in the envelope protein of dengue 2 (Jamaica strain 1409)", *Arch Virol* 105:209–221 (1989).

Bauminger, S. & Wilchek, M. "The USe of Carbodiimides in the Preparation of Immunizing Conjugates" *Methods in Enzymology* 70:151–159 (1980).

Coulis, P.A., et al., "Peptide–based immunodiagnosis of retrovirus infections", *Amer Clin Prod Review,* Nov. 1987.

Deubel V., et al., "Nucleotide Sequence and Deduced Amino Acid Sequence of the Nonstructural Proteins of Denque Type 2 Virus, Jamaica Genotype, Comparative Analysis of the Full–Length Genome", *Virology* 165:234–244 (1988).

Falconar, A.K.I., et al., "Production of dimer–specific and dengue virus group cross–reactive mouse monoclonal antibodies to the dengue 2 virus non–structural glycoprotein NS1", *J Gen Virol 72*:961–965 (1991).

Fu, J., et al. "Full–Length cDNA Sequence of Dengue Type 1 Virus (Singapore Strain S275/90)", *Virology* 188:953–958 (1992).

Geysen, H.M., et al., "Strategies for epitode analysis using peptide synthesis", *J Immun Methods* 102:259–274 (1987).

Geysen, H.M., et al., "Use of peptide synthesis to probe viral antigens for epitopes to a resolution of a single amino acid", *Proc Natl Acad Sci USA* 81:3998–4002 (Jul. 1984).

Gnann Jr., J.W., et al., "Diagnosis of AIDS by Using a 12–Amino Acid Peptide Representing an Immunodominant Epitode of the Human Immunodeficiency Virus", *J Infectious Disease* 156(2):261–267 (Aug. 1987).

Heinz, F.X., "Epitope Mapping of Flavivirus Glycoproteins", *Advances in Virus Research,* 31:103–167 (1986).

Henchal, E.A., et al., "Topological Mapping of Unique Epitopes on the Dengue–2 Virus NS1 Protein Using Monoclonal Antibodies", *J Gen Virol* 68: 845–851 (1987).

Hoop, T.P., et al., "Prediction of protein antigenic determinants from amino acid sequences", *Proc Natl Acad Sci USA,* 78(6): 3824–3828 (Jun. 1981).

Innis, B.L., et al., "Identification of Continuous Epitopes of the Envelope Glycoprotein of Dengue Type 2 Virus", *Am J Trop Med Hyg* 40(6):676–687, (1989).

Mackow, E., et al., "The Nucleotide Sequence of Dengue Type 4 Virus: Analysis of Genes Coding for Nonstructural Proteins", *Virology* 159:217–228 (1987).

Mason, P.W., et al., "The antigenic structure of dengue type 1 virus envelope and NS1 proteins expressed in *Escherichia coli*", *J Gen Virol* 71:2107–2114 (1990).

Megret, F., et al., "Use of Recombinant Fusion Proteins and Monoclonal Antibodies to Define Linear and Discontinuous Antigenic Sites on the Dengue Virus Envelope Glycoprotein", *Virology* 187:480–491 (1992).

Osatomi, K. and Sumiyoshi, H., "Complete Nucelotide Sequence of Dengue Type 3 Virus Genome RNA", *Virology* 176:643–647 (1990).

Putnak, J.R., et al., "Functional and Antigenic Domains of the Dengue–2 Virus Nonstructural Glycoprotein NS–1", *Virology* 163:93–103 (1988).

Qu, X., et al., "Immunoreactivity and protective effects in mice of a recombinant dengue 2 Tonga virus NS1 protein produced in a baculovirus expression system", *J Gen Virol* 74:89–97 (1993).

Roehrig, J.T., et al., "Antibodies to Dengue 2 Virus E–Glycoprotein Synthetic Pepetides Identify Antigenic Conformation", *Virology* 177: 668–675 (1990).

Schlesinger, J.J., et al., "Protection of Mice Against Dengue 2 Virus Encephalitis by Immunization with the Dengue 2 Virus Non–structural Glycoprotein NS1", *J Gen Virol* 68:853–857 (1987).

Shirahama, H. and Suzawa, T. "Absorption of bovine serum albumin onto styrene/acrylic acid copolymer latex", *Colloid & Polymer Sci* 263:141–146 (1985).

Songergard–Andersen, J., et al., "Covalently linked peptides for enzyme–linked immunosorbent assay", *J Imm Methods,* 131:99–104 (1990).

"Report of a WHO workshop on synthetic peptides in HIV diagnosis and AIDS–related research, Moscow 24–26 May 1989", World Health Organization Report, *AIDS,* 5:WHO1–WHO9 (1991).

"Dengue haemorrhagic fever: diagnosis, treatment and control", Published by World Health Organization, ISBN 92 4 154209 8 (1986).

Young, P.R., "Antigenic Analysis of Dengue Virus Using Monoclonal Antibodies", *Southeast Asian J Trop Med Public Health,* 21(4) : 646–651 (1990).

Zhang, Y–M, et al., "Immunization of Mice with Dengue Structural Proteins and Nonstructural Protein NS1 Espresses by Baculovirus Recombinant Induces Resistance to Dengue Virus Encephalitis", *J Virol* 62(8):3024–3031 (1988).

*Primary Examiner*—Laurie Scheiner

*Attorney, Agent, or Firm*—Allen A. Brookes; Carol A. Stratford

[57] ABSTRACT

Peptide antigens derived from the dengue virus type-2 glycoprotein NS1 are provided. The peptide antigens are specifically immunoreactive with sera from individuals infected with the dengue virus. The antigens are useful as diagnostic tools in determining whether an individual has been or is infected with dengue virus, and for discriminating between infection with dengue virus and infection with related flaviviruses. The antigens are also useful in vaccine compositions for immunizing individuals against infection with the dengue virus.

7 Claims, 4 Drawing Sheets

Fig. 1
prM
NS1
NS2A
NS2B
NS3
ns4a
ns4b
NS5

Dengue Virus Genomic Organization

Asp Ser Gly Cys Val Val Ser Trp Lys Asn Lys Glu Leu Lys Cys Gly
1 5 10 15

Ser Gly Ile Phe Ile Thr Asp Asn Val His Thr Trp Thr Glu Gln Tyr
20 25 30

Lys Phe Gln Pro Glu Ser Pro Ser Lys Leu Ala Ser Ala Ile Gln Lys
35 40 45

Ala His Glu Glu Gly Ile Cys Gly Ile Arg Ser Val Thr Arg Leu Glu
50 55 60

Asn Leu Met Trp Lys Gln Ile Thr Pro Glu Leu Asn His Ile Leu Ser
65 70 75 80

Glu Asn Glu Val Lys Leu Thr Ile Met Thr Gly Asp Ile Lys Gly Ile
85 90 95

Met Gln Ala Gly Lys Arg Ser Leu Arg Pro Gln Pro Thr Glu Leu Lys
100 105 110

Tyr Ser Trp Lys Thr Trp Gly Lys Ala Lys Met Leu Ser Thr Glu Ser
115 120 125

His Asn Gln Thr Phe Leu Ile Asp Gly Pro Glu Thr Ala Glu Cys Pro
130 135 140

Asn Thr Asn Arg Ala Trp Asn Ser Leu Glu Val Glu Asp Tyr Gly Phe
145 150 155 160

Gly Val Phe Thr Thr Asn Ile Trp Leu Lys Leu Arg Glu Lys Gln Asp
165 170 175

Val Phe Cys Asp Ser Lys Leu Met Ser Ala Ala Ile Lys Asp Asn Arg
180 185 190

Ala Val His Ala Asp Met Gly Tyr Trp Ile Glu Ser Ala Leu Asn Asp
195 200 205

Thr Trp Lys Met Glu Lys Ala Ser Phe Ile Glu Val Lys Ser Cys His
210 215 220

Trp Pro Lys Ser His Thr Leu Trp Ser Asn Gly Val Leu Glu Ser Glu
225 230 235 240

Met Ile Ile Pro Lys Asn Phe Ala Gly Pro Val Ser Gln His Asn Tyr
245 250 255

Arg Pro Gly Tyr His Thr Gln Thr Ala Gly Pro Trp His Leu Gly Lys
260 265 270

Leu Glu Met Asp Phe Asp Phe Cys Glu Gly Thr Thr Val Val Val Thr
275 280 285

Glu Asp Cys Gly Asn Arg Gly Pro Ser Leu Arg Thr Thr Thr Ala Ser
290 295 300

Gly Lys Leu Ile Thr Glu Trp Cys Cys Arg Ser Cys Thr Leu Pro Pro
305 310 315 320

Leu Arg Tyr Arg Gly Glu Asp Gly Cys Trp Tyr Gly Met Glu Ile Arg
325 330 335

Pro Leu Lys Glu Lys Glu Glu Asn Leu Val Asn Ser Leu Val Thr Ala
340 345 350

Fig 2

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:

( A ) LENGTH: 15 amino acids ( B ) TYPE: amino acid
( C ) STRANDEDNESS: single
( D ) TOPOLOGY: linear ( i i ) MOLECULE TYPE: peptide ( i i i ) HYPOTHETICAL: NO ( v i ) ORIGINAL SOURCE:
( C ) INDIVIDUAL ISOLATE: LPS 122

( x i ) SEQUENCE DESCRIPTION: SEQ ID NO:1:

Tyr Ser Trp Lys Thr Trp Gly Lys Ala Lys Met Leu Ser Thr Glu
1 5 10 15

( 2 ) INFORMATION FOR SEQ ID NO:2:

( i ) SEQUENCE CHARACTERISTICS:
( A ) LENGTH: 26 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v i ) ORIGINAL SOURCE:
( C ) INDIVIDUAL ISOLATE: LPS 177

( x i ) SEQUENCE DESCRIPTION: SEQ ID NO:2:

Ser Leu Arg Pro Gln Pro Thr Glu Leu Lys Tyr Ser Trp Lys Thr Trp
1 5 10 15

Gly Lys Ala Lys Met Leu Ser Thr Glu Ser
20 25

( 2 ) INFORMATION FOR SEQ ID NO:3:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v i ) ORIGINAL SOURCE:
( C ) INDIVIDUAL ISOLATE: LPS 213

( x i ) SEQUENCE DESCRIPTION: SEQ ID NO:3:

Ala Gly Pro Val Ser Gln His Asn Tyr Arg Pro Gly Tyr His Thr Gln
1 5 10 15

Thr Ala Gly Pro Trp His Leu Gly
20

( 2 ) INFORMATION FOR SEQ ID NO:4:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v i ) ORIGINAL SOURCE:
( C ) INDIVIDUAL ISOLATE: Dengue 2, NS1 (83-91)

( x i ) SEQUENCE DESCRIPTION: SEQ ID NO:4:

Glu Val Lys Leu Thr Ile Met Thr Gly
1 5

( 2 ) INFORMATION FOR SEQ ID NO:5:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v i ) ORIGINAL SOURCE:
( C ) INDIVIDUAL ISOLATE: Dengue 2, NS1 (95-103)

( x i ) SEQUENCE DESCRIPTION: SEQ ID NO:5:

Gly Ile Met Gln Ala Gly Lys Arg Ser
1 5

( 2 ) INFORMATION FOR SEQ ID NO:6:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v i ) ORIGINAL SOURCE:
( C ) INDIVIDUAL ISOLATE: Dengue 2, NS1 (101-109)

( x i ) SEQUENCE DESCRIPTION: SEQ ID NO:6:

Lys Arg Ser Leu Arg Pro Gln Pro Thr
1 5

( 2 ) INFORMATION FOR SEQ ID NO:7:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v i ) ORIGINAL SOURCE:
( C ) INDIVIDUAL ISOLATE: Dengue 2, NS1 (104-112)

( x i ) SEQUENCE DESCRIPTION: SEQ ID NO:7:

Leu Arg Pro Gln Pro Thr Glu Leu Lys
1 5

( 2 ) INFORMATION FOR SEQ ID NO:8:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO (vi) ORIGINAL SOURCE:
(C) INDIVIDUAL ISOLATE: Dengue 2, NS1 (107-115)

(xi) SEQUENCE DESCRIPTION: SEQ ID NO:8:

Gln Pro Thr Glu Leu Lys Tyr Ser Trp
1 5

(2) INFORMATION FOR SEQ ID NO:9:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (iii) HYPOTHETICAL: NO (vi) ORIGINAL SOURCE:
(C) INDIVIDUAL ISOLATE: Dengue 2, NS1 (110-118)

(xi) SEQUENCE DESCRIPTION: SEQ ID NO:9:

Glu Leu Lys Tyr Ser Trp Lys Thr Trp
1 5

(2) INFORMATION FOR SEQ ID NO:10:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (iii) HYPOTHETICAL: NO (vi) ORIGINAL SOURCE:
(C) INDIVIDUAL ISOLATE: Dengue 2, NS1 (113-121)

(xi) SEQUENCE DESCRIPTION: SEQ ID NO:10:

Tyr Ser Trp Lys Thr Trp Gly Lys Ala
1 5

(2) INFORMATION FOR SEQ ID NO:11:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (iii) HYPOTHETICAL: NO (vi) ORIGINAL SOURCE:
(C) INDIVIDUAL ISOLATE: Dengue 2, NS1 (116-124)

(xi) SEQUENCE DESCRIPTION: SEQ ID NO:11:

Lys Thr Trp Gly Lys Ala Lys Met Leu
1 5

(2) INFORMATION FOR SEQ ID NO:12:

(i) SEQUENCE CHARACTERISTICS:
(A) LENGTH: 9 amino acids
(B) TYPE: amino acid
(C) STRANDEDNESS: single
(D) TOPOLOGY: linear ( i i ) MOLECULE TYPE: peptide ( i i i ) HYPOTHETICAL: NO ( v i ) ORIGINAL SOURCE:
( C ) INDIVIDUAL ISOLATE: Dengue 2, NS1 (119-127)

( x i ) SEQUENCE DESCRIPTION: SEQ ID NO:12:

Gly Lys Ala Lys Met Leu Ser Thr Glu
1 5

( 2 ) INFORMATION FOR SEQ ID NO:13:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v i ) ORIGINAL SOURCE:
( C ) INDIVIDUAL ISOLATE: Dengue 2, NS1 (122-130)

( x i ) SEQUENCE DESCRIPTION: SEQ ID NO:13:

Lys Met Leu Ser Thr Glu Ser His Asn
1 5

( 2 ) INFORMATION FOR SEQ ID NO:14:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v i ) ORIGINAL SOURCE:
( C ) INDIVIDUAL ISOLATE: Dengue 2, NS1 (191-199)

( x i ) SEQUENCE DESCRIPTION: SEQ ID NO:14:

Asn Arg Ala Val His Ala Asp Met Gly
1 5

( 2 ) INFORMATION FOR SEQ ID NO:15:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v i ) ORIGINAL SOURCE:
( C ) INDIVIDUAL ISOLATE: Dengue 2, NS1 (221-229)

( x i ) SEQUENCE DESCRIPTION: SEQ ID NO:15:

Lys Ser Cys His Trp Pro Lys Ser His
1 5

( 2 ) INFORMATION FOR SEQ ID NO:16:

( i ) SEQUENCE CHARACTERISTICS:

( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v i ) ORIGINAL SOURCE:
( C ) INDIVIDUAL ISOLATE: Dengue 2, NS1 (248-256)

( x i ) SEQUENCE DESCRIPTION: SEQ ID NO:16:

Ala Gly Pro Val Ser Gln His Asn Tyr
1 5

( 2 ) INFORMATION FOR SEQ ID NO:17:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v i ) ORIGINAL SOURCE:
( C ) INDIVIDUAL ISOLATE: Dengue 2, NS1 (263-271)

( x i ) SEQUENCE DESCRIPTION: SEQ ID NO:17:

Gln Thr Ala Gly Pro Trp His Leu Gly
1 5

( 2 ) INFORMATION FOR SEQ ID NO:18:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v i ) ORIGINAL SOURCE:
( C ) INDIVIDUAL ISOLATE: Dengue 2, NS1 (296-304)

( x i ) SEQUENCE DESCRIPTION: SEQ ID NO:18:

Pro Ser Leu Arg Thr Thr Thr Ala Ser
1 5

( 2 ) INFORMATION FOR SEQ ID NO:19:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v i ) ORIGINAL SOURCE:
( C ) INDIVIDUAL ISOLATE: Dengue 2, NS1 (299-307)

( x i ) SEQUENCE DESCRIPTION: SEQ ID NO:19:

Arg Thr Thr Thr Ala Ser Gly Lys Leu
1 5

DENGUE VIRUS PEPTIDES AND METHODS

FIELD OF THE INVENTION

This invention relates to epitopes of the dengue virus useful in diagnostic methods, assays and vaccines for dengue virus infection in humans.

REFERENCES

Aaskov, J. G. et al., Arch. Virol. 105:209 (1989).

Bauminger, S. et al., Methods Enzymol. 70:151 (1980).

Coulis, P. A. et al., Amer. Clin. Products Review (1987).

Deubel, V. et al., Virology 165:234 (1988).

Fu, J. et al, Virology 188:953 (1992).

Geysen, H. M. et al., Proc. Nat. Acad. Sci. 81:3998 (1984).

Geysen, H. M. et al., J. Imm. Methods 102:259 (1987).

Gnann, J. W. et al., J. Inf. Diseases 156(2):261 (1987).

Hopp, T. P. et al., Proc. Nat. Acad. Sci. USA 78:3824 (1981).

Innis, B. L. et al., Am. J. Trop. Med. 40(6):676 (1989).

Mackow, E. et al., Virology 159:217 (1987).

Mason, P. W. et al., J. Gen. Virology 71:2107 (1990).

Megret, F. et al., Virology 187:480 (1992).

Merrifield, R. B., J. Amer. Chem. Soc. 85:2149 (1963).

Osatomi, K. et al., Virology 176:643 (1990).

Putnak, J. R. et al., Virology 163:93 (1988).

Qu, X. et al., J. Gen. Virology 74:89 (1993).

Roehrig, J. T. et al., Virology 177:668 (1990).

Schlesinger, J. J. et al., J. Gen. Virology 68:853 (1987).

Shirahama, H. et al., Colloid. Polym. Sci. 263:141 (1985).

Sonergard-Andersen, J. et al., J. Imm. Methods 131:99 (1990).

Stewart J. M., et al., Solid Phase Peptide Synthesis, Second Ed., Pierce Chemical Co., USA, (1984).

World Health Organization. Dengue haemorrhagic fever: diagnosis, treatment and control. WHO, ISBN 92-4-154209-8 (1986).

World Health Organization. Weekly Epidemiological Record 64(23):175 (1989).

Zhang, Y-M. et al., J. Virology 62(8):3027 (1988).

BACKGROUND OF THE INVENTION

Dengue viruses are causative agents of dengue fever/dengue hemorrhagic fever. Infection with dengue viruses is a major public health problem in tropical countries, especially in South East Asia and the Western Pacific, but recently outbreaks have occurred in the Americas. As the dengue virus is transmitted to humans via the *Aedes aegypti* mosquito, it is not unexpected that the tropical and subtropical countries, in particular those in South East Asia, are highly endemic for dengue.

A major concern and an increasing problem for public health officials has been the occurrence of severe complications arising from dengue viral infection. Both dengue hemorrhagic fever (DHF) and shock syndromes (DSS) are clinical outcomes related to the presence of pre-existing immunity to a heterologous dengue virus serotype. Dengue Haemorrhagic Fever is initially characterized by a minor febrile illness lasting 3–5 days. The patient may deteriorate at defervescence into the next phase of the syndrome with hemostatic disorders, and increased vascular permeability frequently accompanied by internal bleeding and shock. As many as 1.5 million children are reported to have been hospitalized with 33,000 deaths from this syndrome since it was first recognized in Thailand in the 1950's (World Health Organization 1989). DHF/DSS has since continued to persist in South Asia. In another part of the tropical belt, a crippling and devastating outbreak of DHF/DSS occurred in 1981 in Cuba, resulting in 116,000 hospitalized cases (1% of the total population) within a 3 month period. More recent reports for 1987 reveal over 7,292 cases and 222 deaths in Burma, 22,765 cases and 1,039 deaths in Indonesia and 171,630 cases and 896 deaths in Thailand (2). Recent mini outbreaks have also been reported in India, Maldives, Sri Lanka and the South Pacific Islands.

Increased and easier access to travel has probably contributed to this increasing occurrence of DHF/DSS. With modern air travel a viremic person can easily transport the dengue virus from an endemic region to a locality known to be receptive to the virus (presence of *Aedes aegypti* mosquitos) within one day. Thus Dengue outbreaks can pose major problems to public health in many countries.

Dengue outbreaks are usually associated with the density of mosquito vectors, in particular *Aedes aegypti.* Thus control measures typically involve a good dengue surveillance program allowing for early detection of outbreaks and prompt application of measures to control mosquito activity.

Dengue viruses can be divided into 4 serotypes which are antigenically very similar to each other but differ enough to elicit only partial cross-protection after infection by one serotype. Such an infection by one serotype therefore does not provide life-long immunity to the other serotypes (World Heath Organization, 1986). The differences between the 4 serotypes are also noted at the genetic level; i.e., nucleotide and amino acid sequences which have been determined, deduced and made available (Mackow 1987; Deubel 1988; Osatomi 1990; Fu 1992).

There exist reports of identification of epitopes on the structural glycoprotein E (Innis 1989; Aaskov 1989; Roehrig 1990; Megret 1992). Studies have also shown the induction of protective immunity by the glycoprotein NS1 (Schlessinger 1987; Zhang 1988; Qu 1993). However, relatively little has been studied to define the antigenic regions with the latter glycoprotein NS1, which is highly conserved in all flaviviruses (Deubel 1988), and is believed to be one of the important candidates for vaccine development (Mason 1990).

The recognition of any increase in dengue activity is culled from an active surveillance program involving:

a) Surveillance of fever cases b) Seasonal surveillance of Aedes vectors c) Serological and virological surveillance involving laboratory testing of persons suspected to be infected with the dengue virus.

In laboratory diagnosis, a rapid turn around time in test results is necessary so that relevant public health officials can be alerted to activate their mosquito control programs. Undoubtedly a long term solution to the control of dengue viral infection and its debilitating clinical outcomes will require the development of an effective vaccine. Progress has been slow as any potential dengue vaccine must be able to provide complete protection against all 4 serotypes. Incomplete protection will leave the individual at risk for DHF/DSS. Such problems have not been previously encountered in vaccine development for other diseases. It is thus to be expected that new mechanisms of viral pathogenesis will be revealed when a successful dengue vaccine can be developed.

Current laboratory test procedures for detection of dengue virus infection utilize dengue antigens from tissue culture or infected mouse brains. Although tests which utilize such virus antigens will be highly sensitive, the tests will lack specificity. Furthermore, yields of antigens from tissue culture are often unreliable and thus are not suited for large scale commercialization. Although antigens from infected mouse brains yield larger quantities, long and involved purification procedures are required. Dengue viral antigens obtained from tissue culture or mouse brains will also not provide distinction between the various dengue serotypes nor related viruses due to extensive cross-reactivity of viral antigens.

The increasing occurrence of severe complications arising from dengue viral infection including dengue hemorrhagic fever (DHF) and dengue shock syndrome (DSS) is a major problem for public health officials. The dengue virus is endemic in many tropical and subtropical countries and dengue fever is potentially a problem wherever the *Aedes aegypti* mosquito vector may be found. Surveillance programs involving laboratory diagnosis of persons infected with the dengue virus as well as suitable vaccines are necessary for controlling dengue outbreaks. Current laboratory tests are non-specific and unreliable due to the limited availability of suitable dengue antigen.

A diagnostic test that is amenable to large scale screenings and is sensitive enough to differentiate infection with dengue virus from infection with closely related flaviviruses has yet to be developed. The development of such a test which contains dengue antigens that are easily and rapidly obtained with consistent quantities and quality is needed. The test should allow ease of performance in laboratories located in rural areas of tropical and subtropical countries where dengue activity is most likely to be seen.

SUMMARY OF THE INVENTION

It would therefore be useful, for diagnosing dengue virus infection, to provide one or more dengue peptide antigens which are immunoreactive with sera from individuals known to be infected with dengue virus, including those with dengue hemorrhagic fever and/or dengue shock syndrome, and which may be specifically diagnostic of dengue infection. Such antigen(s) could be used in either a simple solid phase or homogeneous antibody-binding assay for rapid determination of antibodies which are diagnostic of dengue virus infection. It is one general object of the invention to provide dengue peptide antigens which are specific for serum from individuals infected with dengue virus.

Another object of the invention is to provide a simple, rapid, relatively inexpensive immunoassay which uses such antigen(s).

The present invention includes peptide antigens which are (a) derived from dengue virus protein NS1 and (b) immunoreactive with serum from individuals infected with dengue virus. One such antigen is preferably derived from the amino acid sequence: Ser-Leu-Arg-Pro-Gln-Pro-Thr-Glu-Leu-Lys-Tyr-Ser-Trp-Lys-Thr-Trp-Gly-Lys-Ala-Lys-Met-Leu-Ser-Thr-Glu-Ser (SEQ ID NO:2). A second antigen is preferably derived from the amino acid sequence: Ala-Gly-Pro-Val-Ser-Gln-His-Asn-Tyr-Arg-Pro-Gly-Tyr-His-Thr-Gln-Thr-Ala-Gly-Pro-Trp-His-Leu-Gly (SEQ ID NO:3).

The invention also includes a system and method for detecting dengue virus infection in a test individual. In the detecting method, one or more antigens of the type described are reacted with serum from the test individual, and then examined for the presence of bound antibody. The assay system may be a solid phase type, in which the antigen(s) is carried on a solid support, or a homogeneous system, in which the antigen(s) is associated with a reporter, where antibody binding to the antigen modulates the reporter signal when detected.

In still another aspect, the invention includes a vaccine for immunizing an individual against dengue hemorrhagic fever and/or dengue shock syndrome. The vaccine includes one or more peptides of the type described, in a pharmaceutically acceptable adjuvant.

These and other objects and features of the invention will become more fully understood when the following detailed description of the invention is read in conjunction with the accompanying figures.

BRIEF DESCRIPTION OF THE FIGURES

2. FIG. 2 contains the predicted amino acid sequence of the NS1 glycoprotein.

DETAILED DESCRIPTION OF THE INVENTION

I. Definitions

The term "antigen" refers to a molecule which is specifically recognized and bound by antibodies contained in human sera. An antigen which elicits an immune response in an organism, as evidenced by production of specific antibodies within the organism is termed an "immunogen." The terms "immunogenic region" or "epitope" are used interchangeably herein to indicate that region of an antigen which is specifically recognized by an antibody in human sera.

The "epitope formed by" a given amino acid sequence is the epitope produced by the secondary/tertiary structure of that sequence in aqueous solution.

The "antigen binding site" is that region of an antibody molecule contained within the variable regions of the antibody which directly participates in binding the antigen.

A specified "peptide antigen containing the epitope formed by" a specified amino acid sequence includes the specified sequence itself or a portion thereof which is sufficient to define the epitope present in the specified sequence, as evidenced by immunoreactivity to an antibody contained in a human sera sample. The specified peptide antigen may include amino acid substitutions which preserve the epitope.

II. Fine Mapping of NS1 Linear Antigenic Sites

This section describes experiments carried out to identify the peptide regions which are immunoreactive with human sera from individuals infected with dengue virus. In general, to determine the epitope specifically or "fine-map" the antigen specificity of an antibody or serum sample, it is necessary to synthesize or recombinantly express specific peptide portions of the antigen. Such peptides can then be employed in solid phase or liquid competition assays, such as ELISA or RIA, to determine specificity of binding.

Figure 1:
FIG. 1 illustrates the genomic organization of the dengue virus.

A slight modification of the PEPSCAN method, which has previously been used for epitope identifications of dengue virus in the envelope region (Aaskov 1989; Innis 1989), was used to initially identify linear epitopes on the dengue virus polypeptide NS1. The genomic organization and relative location of NS1 is illustrated in FIG. 1.

A. NS1 Nonameric Peptide Synthesis

Peptide antigens which are useful in determining epitopic specificity of a human serum sample are formed by any of several methods which are effective to produce small; defined portions of the parent antigenic protein. Thus, limited proteolysis of a viral protein, followed by separation and purification of fragments, or chemical or recombinant synthesis of such defined fragments, for use as components of a fusion protein or alone, are all means of producing peptide antigens useful in fine-mapping.

Peptides of less than about 50 amino acid residues can be synthesized using chemical solid-phase synthetic methods, such as the method described in Example 1, or by commercially available synthesizers as is described in Example 3B. These methods are preferred and particularly useful when the entire amino acid sequence is known, either directly, through amino acid sequencing, or through deduction based on nucleic acid sequence.

In the chemically synthesized method of Example 1, one hundred and fifteen (115) overlapping peptides were synthesized, based on the deduced amino acid sequence of dengue virus type-2 from a published RNA sequence (Deubel et al., 1988) to span the NS1 protein. The peptides were synthesized on polyethylene pins using the commercially available Epitope Scanning Kit (Mimotopes, Australia). The synthesis procedure has been described by others (Geysen et al. 1984, 1987).

Briefly, peptides which are nine amino acids in length and which overlap by six residues were synthesized to span the C-terminal 351 amino acids of the 352 amino acid NS1 polypeptide, using active esters (pentafluorophenyl derivatives) of Fmoc-L-amino acids. The amino acid sequences of each peptide may be found in Table 7. Prior to the synthesis reaction, blocks of pins were deprotected using 20%. piperidine in dimethylformamide (DMF) and subsequently washed with DMF and Methanol (MeOH) before adding amino acids. The couplings of amino acids were carried out in DMF in the presence of the catalyst hydroxybenzotriazole (Hobt). Again, washes using DMF and MeOH were performed after coupling. These deprotection, washing, coupling and washing steps were repeated until all the amino acids coupled; i.e., until a nonapeptide was synthesized on each pin. The on-pin peptides were then subject to acetylation of the terminal amino groups using acetic anhydride. The peptides underwent an additional side chain deprotection and neutralization step using trifluoroacetic acid, phenol and ethanedithiol prior to epitope scanning assays.

Alternatively, recombinant production of nonameric peptides is possible. Oligomeric nucleotides which encode the desired peptide are produced by well known methods such as chemical synthesis. The oligomers are then ligated to a suitable expression vector, for example pBluescript® (Stratagene). An appropriate host, for example, the *E. coli* strain "XL-1 Blue™" (Stratagene), is then transformed with the expression vector. The host is subsequently cultured under conditions suitable for expression of the peptide encoded by the ligated oligomer. Culture conditions suitable for expressing beta-galactosidase fusion proteins in pBluescript®, for example, include the presence of isopropylthiogalactoside (IPTG). The resulting peptide may then be purified, especially easily when expressed as a fusion protein, wherein a monoclonal antibody specific for the fusion partner may be employed in the purification reaction.

When using short peptides, less than about 50 amino acids, solid phase synthesis is relatively inexpensive and less time consuming than the recombinant method and is therefore preferred.

B. Screening NS1 Peptides with Human Sera

Following production of peptide antigens, in accordance with the invention, sera taken from dengue infected individuals are tested for their ability to bind to such antigens.

1. Dengue-Infected Human Sera Samples for Screening Peptides

Dengue viruses occur as four serotypes, DEN 1, DEN 2, DEN 3, and DEN 4. Two types of serological response patterns are identified in dengue infected individuals (World Health Organization 1986). Individuals who have never been exposed to flavivirus infections or vaccines (Japanese Encephalitis Virus (JEV) or Yellow Fever) will show a PRIMARY response. This is characterized by a slow rise in antibody titre which is specific against the infecting virus. Individuals who have had a previous flavivirus infection or vaccination (JEV or Yellow fever), or a previous infection with a different dengue serotype will manifest a SECONDARY response. This response is characterized by a rapid rise in dengue antibody titre.

Various laboratory tests are available for diagnosis of dengue infections. Often laboratory diagnosis of dengue infection is based on results obtained from a combination of methods including: (a) viral isolation; (b) antigen detection, and (c) various serological tests with hemagglutination inhibition (HI) as the gold standard. An ultimate diagnosis of dengue virus infection rests on the isolation of the virus from serum of a patient via tissue culture procedures. Isolation rates are usually low because the technique requires proper collection, storage and shipment of specimens to the laboratory. A high level of technical skill is required for such viral isolation work. Thus a negative result does not necessarily mean that the virus is not present.

Another routine method for laboratory diagnosis of dengue infection is to demonstrate a rising titre of anti-dengue antibodies in the serum. This classical serological method relies on the ability of dengue agglutinins to bind goose red blood cells causing these cells to clump. The Hemagglutination Inhibition (HI) test then relies on antibodies (present in infected patient sera) to inhibit the agglutination of goose cells. This test requires the use of hemagglutinins made from 4 dengue serotypes as well as agglutinins of the closely related Japanese Encephalitis virus. Paired sera is required in the test and a positive diagnosis is made if there is a four-fold rise in antibody titre in the second sample.

Current test procedures rely on dengue antigens collected from tissue culture or infected mouse brains. Antigens obtained in this way will not provide distinction between the various flaviviruses due to extensive cross-reactivity of viral antigens to closely related flaviviruses. However, specificity may be increased by combining the HI test with one or more of the tests above.

Seven serum samples from Singapore were used for mapping of the NS1 epitopes. Characterization of the samples are outlined in Table 1. These include two samples taken from patients in convalescent stage with Hemagglutination Inhibition (HI) test titres greater than 10240, two samples taken from patients in acute stage of infection with HI titres of 2560, and two samples that react strongly to the commercially available "Dengue Blot" test kit (Diagnostic Biotechnology, Singapore) and to an IgM captured ELISA. In addition, a patient serum sample from Indonesia with dengue serotype-2 infection as defined by the virus isolation assay was also used.

TABLE 1

Human Sera Samples used in the Epitope Mapping Assays

| | | TEST | | | |
|---|---|---|---|---|---|
| | | | Dengue | HI titres | |
| Serum No. | Specimen | IgM EIA | Blot | DEN 1 | DEN 2 |
| SGH1923 | Single | Positive | Positive | ND | ND |
| SGH1924 | Single | Positive | Positive | ND | ND |
| SGH2896 | Acute | Positive | Positive | 1:2560 | 1:2560 |
| SGH3085 | Acute | Negative | Positive | 1:640 | 1:2560 |
| SGH2778 | Conval. | Positive | Positive | 1:10240 | 1:10240 |
| SGH3141 | Conval. | ND | ND | 1:2560 | 1:10240 |
| 91035A | N.A. | N.A. | N.A. | N.A. | N.A. |

Note. 91035A is a patient serum sample with dengue type-2 infection from Indonesia confirmed by virus isolation.

2. Peptide Screening

Briefly, on-pin peptides were screened for their antigenicities using the enzyme-linked immunosorbent assay (ELISA) procedure accompanying the Epitope Scanning Kit (Mimotopes, Australia) but with slight modifications as in Example 2. The pins with peptides permanently coupled onto them were blocked with a super cocktail of ovalbumin, bovine serum albumin (BSA) and polyoxiethylenesorbitan monolaurate (Tween 20™) in phosphate buffered saline (PBS), for an hour prior to immunoassay. The pins were then incubated with sera in the super cocktail overnight at 4° C. and were subsequently washed with PBS/Tween 20™. The pins were further incubated with phosphatase labeled anti-human IgG. After washing again with PBS/Tween 20™, these pins were incubated with the substrate solution for 30 minutes at 37° C. Reaction results were obtained from a plate reader at 405/620 nm. The blocks of pins were regenerated by sonication.

Figure 3:
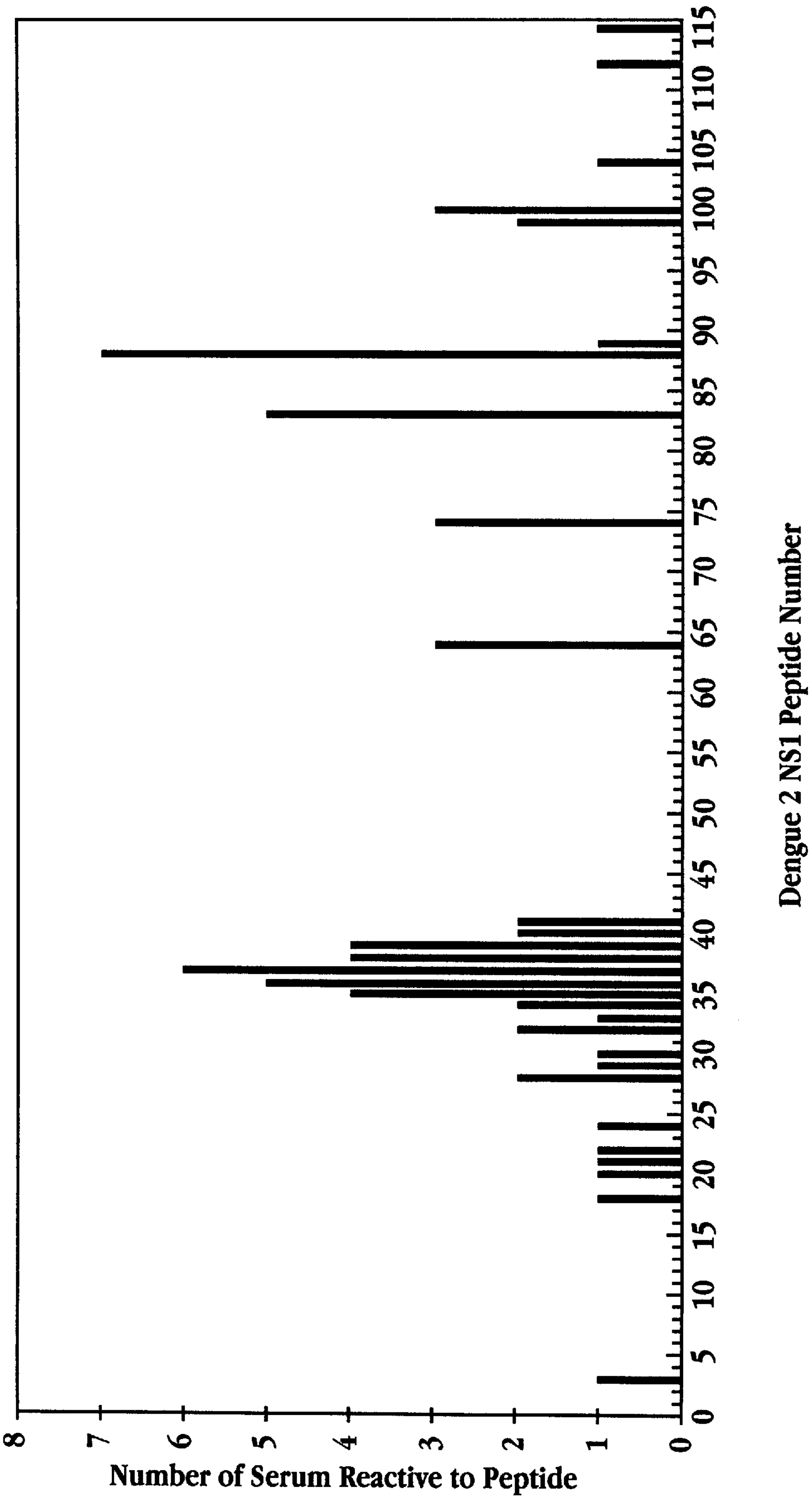
FIG. 3 illustrates the reactivity each of 115 NS1 nonameric peptides showed toward seven sera samples taken from individuals infected with dengue virus.

ELISA results were analyzed by a computer program from the supplier of the Epitope Scanning Kit (Mimotopes, Australia). From the total of 115 overlapping nonapeptides, 16 were found to react with two or more serum samples as identified by computer program (FIG. 3 and Table 2 below). Amongst the reactive peptides, eight were in a sequential order covering the region of NS1 amino acids 101–130 (KRSLRPQPTELKYSWKTWGKAKMLSTESHN). We have designated this stretch of sequence as Immunoreactive Region A (Site A). Site A contains a particularly reactive nonapeptide (ELKYSWKTW) (SEQ ID NO:9) which is reactive with 6 out of the 7 tested serum samples (Table 2).

The most immunoreactive peptide, however, is not in Site (A) but further to the carboxy terminus. One nonapeptide in particular, amino acids 263–271 (QTAGPWHLG) (SEQ ID NO:17). is recognized by all seven serum samples (Table 2). In addition, there is another fairly reactive sequence recognized by five serum samples which is located at amino acids 248–256 (AGPVSQHNY) (SEQ ID NO:16). These peptides are highly reactive and separated by only six amino acids. This site (248–271) encompassing both highly reactive peptides, therefore, was selected as another potential epitope and designated Immunoreactive Region B (Site B).

TABLE 2

Peptides Reactive with Dengue Infected Human Serum Samples

| Nonapeptide amino acid location | Sequence | Number of Reactive Serum Samples | Potential Antigenic Site |
|---|---|---|---|
| 83–91 | EVKLTIMTG | 2 | |
| 95–103 | GIMQAGKRS | 2 | |
| 101–109 | KRSLRPQPT | 2 | A |
| 104–112 | LRPQPTELK | 4 | A |
| 107–115 | QPTELKYSW | 5 | A |
| 110–118 | ELKYSWKTW | 6 | A |
| 113–121 | YSWKTWGKA | 4 | A |
| 116–124 | KTWGKAKML | 4 | A |
| 119–127 | GKAKMLSTE | 2 | A |
| 122–130 | KMLSTESHN | 2 | A |
| 191–199 | NRAVHADMG | 3 | |
| 221–229 | KSCHWPKSH | 3 | |
| 248–256 | AGPVSQHNY | 5 | B |
| 263–271 | QTAGPWHLG | 7 | B |
| 296–304 | PSLRTTTAS | 2 | |
| 299–307 | RTTTASGKL | 3 | |

III. Larger Peptides Spanning Immunoreactive Regions

This section describes selection and testing of larger peptides which contain many of the immunoreactive nonameric peptide sequences found in localized immunoreactive regions.

A. Peptide selection and synthesis

The epitope screening assay is useful for fine-mapping linear epitopes. It may, however, also be useful to identify and test a more comprehensive immunoreactive region which spans a larger sequence for enhanced reactivity to sera from individuals infected with dengue virus.

Longer peptides encompassing putative immunoreactive regions may be produced in the same way as described above; e.g., degradative, recombinant or synthetic methods. Preferably, peptides useful as immunogens for diagnostics would react with antibodies present in sera collected from individuals infected with any of the four dengue serotypes. Peptides with conserved regions of amino acid sequence are more likely to be recognized by anti-DEN 1, -DEN 2, -DEN 3, and -DEN 4 antisera than peptides derived from divergent areas and, therefore, are preferably selected. Antibodies raised against the NS1 polypeptide putatively cross-reacts with several other flaviviruses. The cross-reactivity is presumably due to certain cross-reactive epitopes encoded by dengue virus as is seen with other viruses. Type-specific epitopes are presumably encoded by NS1 as well (Mason et al., 1990). A smaller peptide derived from a larger, naturally occurring protein is, therefore, more likely to define a dengue specific immunoreactive region. Selecting the smaller peptide eliminates the cross-reactive epitopes common to several flaviviruses contained in the whole protein. It is useful to compare the known or deduced amino acid sequence, therefore, when choosing peptides to produce and test.

Figure 4:
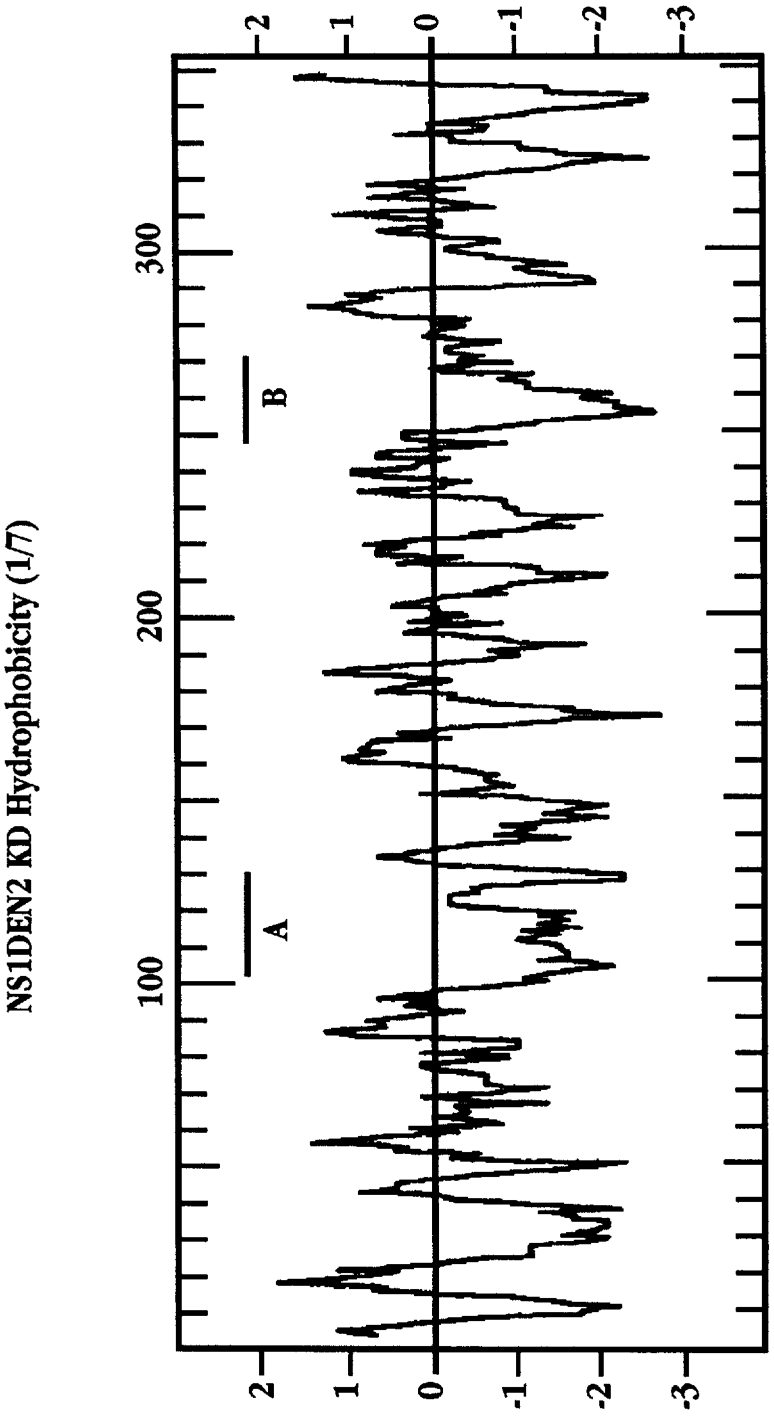
FIG. 4 is a hydropathy profile of the NS1 protein, where positive values on the ordinate indicate hydrophobicity and negative values indicate hydrophilicity. The two Immunoreactive Regions, Site A and Site B, are outlined.

Based on the combined results of mapping, sequence homology comparison and hydrophilicity profile (FIG. 4), three peptides of 15–27 amino acids in length from the NS1 region of dengue virus type-2 where chosen as most likely to encode strong dengue specific epitopes. The peptides were synthesized and are listed in Table 3, below. Peptide LPS122 (aa 113–127 SEQ ID NO:1) which covers the C-terminal 15 amino acid region of Immunoreactive Region A, peptide LPS177 (aa 103–128 SEQ ID NO:2) which covers Immunoreactive Region A, and peptide LPS213 (aa 248–271 SEQ ID NO:3) spanning Immunoreactive Region B, were synthesized using either an automated synthesizer (Model 431A, Applied Biosystems Inc., Foster City, Calif.), or a manual solid-phase synthesis method (Stewart, 1984). In the automated method, a solid-phase peptide synthesis method, developed by Merrifield (1963), was adapted (Users Manual, Applied Biosystems, version 1.12:8/15/89, p14–24) and used in production of the peptides (Example 3). Additionally, two C-terminal lysines were added to the terminus of LPS213 in order to increase the hydrophilicity value and solubility of the peptide.

TABLE 3

Immunogenic Regions Tested and their Homology with other Serotype

| Peptide | Sequence | Homology DEN-1 | DEN-3 | DEN-4 |
|---|---|---|---|---|
| LPS122 | YSWKTWGKAIKLSTE | 67 | 67 | 73 |
| LPS177 | SLRPQPTELKYSWKTWGKAAALSTES | 60 | 72 | 60 |
| LPS213 | AGPVSQHNYRPGYHTQTAGPWHLGKK* | 88 | 92 | 84 |

*LPS213 - two C-terminal Lysines were added to increase the hydrophilicity value and the solubility of the peptide B. Testing Immunoreactivity of Larger Peptides with Human Sera 1. Sera and Their Sources Human sera with dengue hemagglutination inhibition (HI) antibodies were obtained from clinical specimens in Singapore General Hospital. These were convalescent sera with high HI titres of 10240 and paired sera with convalescent titre not less than 1280 but with 4 fold rise in HI titres. Human sera with dengue type-1 and type-2 infections as confirmed by virus isolations were obtained from Malaysia and Indonesia. In addition, etiologically confirmed Japanese Encephalitis Virus (JEV) infected serum specimens were obtained from Malaysia. These sera were additionally tested using IgM capture ELISAs and immunoblot assays for both IgM and IgG antibodies to JEV. Normal human sera was purchased from Peninsula Memorial Blood Bank, USA. These donor sera were additionally examined using an in-house Dengue Blot and confirmed to be negative for dengue.

2. Evaluation of Larger Peptides

Synthetic peptides can be immobilized onto solid supports such as microtitre plates and nitrocellulose membranes. Occasionally, however, problems arise using short, peptides in solid-phase reactions, for example, certain peptides lack adequate binding capabilities, present wrong configurations due to attachments, and/or loosen during the mechanics of the assay process (Sonergard-Andersen 1990). One approach to alleviating this problem is to covalently couple the peptides to a larger protein such as Bovine Serum Albumin (BSA) which is known to attach to the solid phase (Shirahama 1985).

In the present invention, peptides were coupled to BSA using carbodiimides as in Example 4. Next, coupled and uncoupled peptides were immobilized on nitrocellulose membranes (Sacotorius, F. R. Germany) with the Immunetics Miniblotter system (Immunetics, Cambridge, Mass.) as in Example 5. The membrane bound peptides were then blocked with a milk blocking solution, washed and dried. Test strips were cut and the strips were incubated with the dengue virus infected human sera samples as defined by the hemagglutination inhibition (HI) assay and by enzyme immuno-assay (EIA). The assay results are provided in Table 4 below.

TABLE 4

Reactivities of Synthetic Peptides to Dengue (+) Sera

| Specimen | Reactivity (no. positive/total no. tested) LPS122 | LPS177 | LPS122-BSA | LPS177-BSA |
|---|---|---|---|---|
| Acute | ND | 3% (1/33) | 42% (14/33) | 49% (16/33) |
| Conval. | 20% (3/15)* | 37% (16/43) | 77% (33/43) | 84% (36/43) |
| Donor | ND | 1% (1/87) | 14% (12/87) | 12% (10/87) |

*Sera tested are from an earlier collection (HI > 2560) but same source (Singapore General Hospital, Singapore)

As described in Table 4 above, peptide LPS122 was recognized by about 20% of the human dengue-infected sera tested whereas the longer peptide, LPS177, was recognized by more (37%), of the sera tested. Peptides in the coupled form react to the human dengue sera better than their uncoupled counterparts do. Peptide LPS122-BSA was reactive with 77%. of the human dengue-infected sera tested and peptide LPS177-BSA was reactive with 84% of the human dengue-infected sera tested. All the peptides, coupled or not, are consistently recognized by the convalescent specimens better than the acute specimens. This might be explained by the fact that no fundamental modification to the primary sequences of the coupled peptides has taken place. The coupling process simply mimics the situation in the mapping assays; i.e., peptides are attached to the solid phase by their C-terminus.

Peptide LPS213 failed to react with tested sera either coupled with BSA or not. Region B may still encode an important epitope: the LPS213 peptide contains one of the most immunoreactive nonapeptides as defined by the epitope mapping assay (Table 2); and LPS213 comes from a sequence that is highly conserved (84–92% homology) with other dengue serotypes (Table 3). This peptide contains many non-polar residues and has a rather low hydrophilicity value (−0.3 Kcal), average values of 25 amino acids based on the Hopp-Woods method (Hopp-Woods, 1981), which may have contributed to the unexpectedly poor results. To facilitate solubility, two lysine residues were added to the C-terminus of the peptide during the synthesis process which may account for some unexpected deleterious effect.

Peptides LPS122 and LPS177 conjugated to BSA were further studied with paired patient sera characterized by viral isolation. The immunoassays were carried out as described above and in Example 5, below. The results of these screenings are set out in Table 5, below.

TABLE 5

Reactivities of Dengue (Type 1, 2) Paired Serum to LPS122 and 177

| | | | | Reactivity (*) | |
|---|---|---|---|---|---|
| Sera No. | Grade | Imm. Resp. | Isolation | LPS122 | LPS177 |
| D89 601 | DHF II | Primary | Den1 | – | – |
| D88 288 | DHF II | Primary | Den1 | – | – |
| D89 597 | DHF I | Primary | Den2 | – | – |
| D88 285 | DHF I | Secondary | Den1 | + (1,2) | ++ (1,2) |
| D89 541 | DHF III | Secondary | Den1 | – | + (2) |
| D89 557 | DHF III | Secondary | Den1 | – | + (1,2) |
| D98 634 | DHF I | Secondary | Den1 | – | – |
| D88 292 | DHF II | Secondary | Den2 | – | – |
| D89 551 | DHF IV | Secondary | Den2 | + (2) | + (2) |
| D89 537 | DHF I | Secondary | Den2 | – | – |
| D89 539 | DHF I | Secondary | Den2 | – | – |
| D89 575 | DHF IV | Secondary | Den2 | – | + (2) |
| D89 633 | DF | Secondary | Den2 | – | + (2) |

*1 = acute, 2 = convalescent specimen; LPS peptides are BSA conjugated

Results in Table 5 show that LPS177-BSA is readily recognized by sera with dengue serotype-1 infection despite the fact that the peptide was synthesized based on a dengue serotype-2 sequence and has only 60% homology with the same region in dengue-1. This result suggests that the antigenic site revealed with this approach may be a dengue common (group) epitope.

The study using dengue infected human sera with different serotype infections also shows that the peptides were more readily recognized by the specimens with secondary infections than by those with primary infections (Table 5). This is not surprising because selection probably resulted from the sera used in the epitope mapping assay which are ones with high HI titres and, according to the World Health Organization standard's, belong to secondary infections (World Health Organization, 1986).

3. Reactivity of LPS177 with Japanese Encephalitis Virus Infected Sera.

LPS177 coupled to BSA was tested with a panel of 14 etiologically confirmed JEV positive serum samples. The immunoassays were carried out as described above and in Example 5. As can be seen from Table 6 below, no cross-reactivities were detected with the peptide to twelve samples from 7 patients. The only exception was the paired samples from one particular patient who had a secondary flavivirus infection. In this case, the acute specimen reacted strongly to LPS177-BSA. This specimen, however, was also shown to have antibodies to dengue by a conventional serological test, the "Dengue Blot" IgG assay (Diagnostic Biotechnology, Ltd., Singapore). The data listed in Table 6 demonstrates that the identifed region covered by LPS177 is a dengue specific epitope.

TABLE 6

Reactivities of Japanese Encephalitis Virus Positive Sera to LPS177-BSA

| | | IgM capture ELISA | | | Immunoblot IgG | | | |
|---|---|---|---|---|---|---|---|---|
| Patient | Sample | JE | | DEN | JE | | DEN | Peptide |
| 1 | PK2652 | ++ | > | + | + | = | + | +++ |
| | PK2666 | | | | | | | +/– |
| 2 | PK3570.1 | ++ | > | + | + | > | – | – |
| | PK3570.2 | | | | | | | |
| 3 | PK2136.1 | – | = | – | – | = | – | – |
| | PK2136.2 | + | > | – | – | = | – | – |
| 4 | PK3018.2 | ++ | > | + | ++ | > | = | – |
| | PK3085 | | | | | | | – |
| 5 | PK3030 | ++ | > | + | + | = | + | – |
| | PK3084 | | | | | | | – |
| 6 | PK2985.1 | + | > | – | – | | – | – |
| | PK2985.2 | | | | | | | – |
| 7 | VT1093.2 | + | > | – | – | | – | – |
| 8 | VT1064.1 | + | > | – | – | | – | – |

III. Peptide Antigens for Dengue Assays

This section describes the peptide antigens which are employed in the assay kit, assay method and vaccine described in Section IV below.

A first antigen includes a peptide antigen containing the epitope formed by the amino acid sequence of the LPS122 peptide. A second antigen includes a peptide antigen containing the epitope formed by the amino acid sequence of the LPS177 peptide. A third antigen includes a peptide antigen containing the epitope formed by the amino acid sequence of the LPS213 peptide. The amino acid sequences of these peptides are shown in Table 3.

These peptide antigens can be prepared recombinantly, either as fused proteins or as small recombinant peptides. Alternatively, the peptide antigens can be prepared by conventional solid-phase synthetic methods described above and in Example 3.

Studies conducted in support of the present invention, discussed above, demonstrate that the LPS122 and the LPS177 peptide antigens are specific for dengue virus; i.e., the antigens immunoreact with antibodies present in humans infected with the dengue virus. The antigens, however, may not detect all dengue positive individuals, and may pick up some false positives; e.g., individuals infected with a related flavivirus. As described above, the LPS122 and LPS177 peptide antigens are derived from the NS1 protein of the dengue serotype-2 virus.

More specifically, LPS122 and LPS177 were shown to be selectively reactive with sera from individuals with dengue viral infections; i.e., the antigens immunoreact with antibodies present in humans with dengue viral infections. The antigens, however, may not detect all dengue infections, and may also pick up some flavivirus infections other than dengue or uninfected samples.

Peptide LPS213 is also derived from the NS1 region of the dengue serotype-2, and although non-reactive with dengue infected human sera itself either coupled to BSA or uncoupled, it has been shown to contain regions that are highly immunoreactive with sera from humans infected with the dengue virus. This peptide contains two of the most reactive nonameric peptides (Table 2, above). LPS213 also comes from a sequence which is highly conserved (84–92% homology) with other dengue serotypes; i.e., dengue-1, dengue-3, and dengue-4 (Table 3, above). Furthermore, the two highly reactive nonamers are separated by only six residues. It is probable that the epitope contained in the region is a conformational epitope. The two nonapeptides, therefore, would only be brought together by tertiary structure to achieve natural antigenicity. Being in a linear form as in LPS213, the two nonamer segments are not in their best antigenic conformations and, thus, fail to elicit any antigenicity, as compared to when they are attached on pins.

The small peptide antigens useful in the present invention are taken from regions of relatively high sequence homology between the dengue serotypes and are expected to be dengue specific. That is they are expected to react with sera from an individual infected with any one of the four dengue serotypes but not react with sera from an individual infected with a related virus; i.e., Japanese Encephalitis virus, Yellow Fever virus, West Nile river virus, Murray Valley virus, or the St. Louis Encephalitis virus. In fact when tested, LPS177-BSA did not cross-react with confirmed Japanese Encephalitis virus infected sera. Thus, the short peptides are dengue specific and consequently valuable in the methods and kits of the present invention. In this respect, peptide LPS177, which did not cross-react to the confirmed JE specimens when tested, has been demonstrated to include a dengue specific epitope.

Gene products of dengue virions include the following proteins translated as a single polypeptide and modified post-translationally: 5'-C, prM, M, E, NS1, ns2a, ns2b, NS3, ns4a, ns4b, and NS5-3' as shown in FIG. 1. The virion contains three structural proteins, the core (C) protein which encapsidates the virion RNA, the M protein (derived by cleavage from prM) and the glycoprotein E both of which are associated with the lipid envelope. Glycoproteins prM and NS1 have been shown to play a potentially important role in protection through passive protection experiments using monoclonal antibodies (Kaufman 1989, Henchal 1987). Studies have shown that the nonstructural glycoprotein NS1 of dengue is highly immunogenic and can elicit protective effects in mice (Schlesinger 1987; Shang 1988; and Qu 1993). Existing studies concerning the region, however, are relatively few and somewhat indirect. Putnak (1988) has located antibody binding sites for mouse polyclonal antibodies and for rabbit antiserum in the NS1 region of a dengue type-2 virus. In addition, antigenic domains of NS1 of a dengue type-1 virus were also reported to have been defined using monoclonal antibodies and polyclonal antibodies from HMAF (Mason 1990). Although these studies have provided insight on the reactivity of the region to certain animal antibodies, no information has been given as to how the glycoprotein NS1 responds to human anti-dengue antisera. In this respect, the peptide of the present invention discovered with human anti-dengue antisera provides direct information on which section of the glycoprotein is the antigenic domain recognized by human antibodies. Such novel peptides are therefore useful for the purposes of diagnosis and vaccine development as will be fully understood when read in conjunction with the following section.

IV. Utility

This section describes uses of the antigenic peptides of the invention for diagnosing dengue viral infection, and as a potential vaccine against dengue viral infection.

Various laboratory tests are available for diagnosis of dengue infections. Often laboratory diagnosis of dengue infection is based on results obtained from a combination of methods including; (a) viral isolation, (b) hemagglutination inhibition (HI), (c) IgM capture ELISA, (d) neutralization tests, and (e) complement fixation test. Viral. isolation is difficult resulting in many false negatives. ELISA based tests to detect IgM or IgG antibodies are limited to well equipped laboratories as the reagent preparations are laborious.

The current gold standard for ultimate diagnosis as outlined by the World Health Organization is the hemagglutination inhibition (HI) test. HI relies on the ability of dengue antibodies (present in infected patient sera) to inhibit the agglutination of goose cells caused by dengue virus. This test requires the use of hemagglutinins made from 4 dengue serotypes as well as agglutinins of the closely related Japanese Encephalitis (JE) virus, resulting in laborious reagent preparation time. Paired sera is required in the test and a positive diagnosis is made if there is a four-fold rise in antibody titre in the second sample.

Current test procedures rely on dengue antigens from tissue culture of infected mouse brains. Antigens obtained in this way will not provide distinction between the various flaviviruses due to extensive cross-reactivity of viral antigens to closely related flaviviruses.

A. Diagnostic Methods and Kits

Three basic types of diagnostic applications of the peptide antigens will be described. The first is based on inhibition of complement-mediated, antibody-dependent cytolysis by the peptide. In this method, serum from a test individual is reacted with dengue infected *Aedes aegypti* cultured cells in the presence of complement. The presence of anti-dengue antibody is evidenced by cell lysis, as judged, for example, by trypan blue dye exclusion. Where cell lysis is observed, the specificity of the anti-dengue antibody for the dengue peptide is demonstrated by first reacting the serum with excess peptide, then mixing the serum with the cells in the presence of complement. Antibody specificity is indicated by a substantial decrease in cell lysis. The method can also be used to quantitate the antibody titre in the analyte serum, by titrating the serum with increasing amounts of peptide concentration where a noticeable effect on the extent of cell lysis is first observed.

The second general assay type is a solid-phase immunoassay. In this method, a solid phase reagent having surface-bound peptide is reacted with analyte serum, under conditions which allow antibody binding to the peptide on the reagent. After washing the reagent to remove unbound serum components, the reagent is reacted with reporter-labeled anti-human antibody to bind reporter to the reagent in proportion to the amount of bound anti-dengue antibody on the solid support. The reagent is again washed to remove unbound labeled antibody, and the amount of reporter associated with the reagent is determined. Typically, as in the system described in Example 5, the reporter is an enzyme which is detected by incubating the solid reagent in the presence of a suitable fluorometric or colorimetric substrate. However, radiolabel and other reporters may be used.

After reacting the analyte serum with the solid-phase bound antigen and washing to remove the unbound serum components, one may alternatively use the peptide antigen itself bound to reporter as a detection reagent instead of using an anti-human antibody as a reporter mediator. The competitive assay takes advantage of antibody bivalency. The same reporters may be used in this embodiment of the solid-phase assay as was described above.

Multiple peptides may be used in conjunction or in tandem in each of the assays described above. In addition, reaction to each peptide may be distinguished. For example, in the solid-phase assay described above, two or more different peptides may be bound to solid phase in separate locations so that reaction to each peptide may be quantitated separately. Alternatively, peptide antigens labeled with distinguishable reporters may be used to detect peptides which are interspersed on the solid support.

The solid surface reagent in the above assay is prepared by known techniques for attaching protein material to solid support material, such as polymeric beads, dip sticks, or filter material. These attachment methods generally include non-specific adsorption of the protein to the support or covalent attachment of the protein, typically through a free amine group to a chemically reactive group on the solid support, such as an activated carboxyl, hydroxyl, or aldehyde group.

The third general assay type is a homogeneous assay, in which antibody binding to a solid support produces some change in the reaction medium. Known general types of homogeneous assays proposed heretofore include: (a) spin-labeled reporters, where antibody binding to the antigen is detected by a change in reporter mobility (broadening of the spin splitting peaks); (b) fluorescent reporters, where binding is detected by a change in fluorescence efficiency; (c) enzyme reporters, where antibody binding effects enzyme/substrate interactions such as the system described in Example 2; and (d) liposome-bound reporters, where binding leads to liposome lysis and release of encapsulated reporter. The adaption of these methods to the peptides of the present invention follows conventional methods for preparation of homogeneous assay reagents.

In each of the three general assays described above, the assay method involves reacting the serum from a test individual with the antigen, and examining the antigen for the presence of bound antibody. In the first assay, the examining is done by observing the decrease in antibody-mediated cytolysis, when the antibody is bound to the peptide. In the solid-phase assay, the examining involves attaching a labeled anti-human antibody to the antibody being examined, and measuring the amount of reporter bound to the solid support. And in the third assay type, the examining is done by observing the effect of antibody binding on a homogeneous assay reagent.

B. Peptide Vaccine

The peptide antigens of the invention may also be used as a vaccine, to induce cytotoxic anti-dengue antibodies. Here it is important to note that human sera is cytotoxic to *Aedes aegypti* cells infected with dengue virus in the presence of complement. The peptide is formulated with a suitable carrier/adjuvant and injected at periodic intervals, until a significant titre of cytotoxic anti- dengue antibody is detected in the serum. The vaccine would provide protection, by antibody-mediated cytotoxicity, against dengue infection and resulting diseases.

The following examples illustrate various aspects of the invention, but are in no way intended to limit the scope thereof.

Materials

Serum specimen were obtained from patients with clinical diagnosis of dengue fever or "viral fever" in Singapore General Hospital. Human sera with dengue type 1 or type 2 infections as confirmed by virus isolations were obtained from Malaysia and Indonesia. Japanese Encephalitis Virus infected sera was also obtained from Malaysia. Normal human sera was purchased from Peninsula Memorial Blood Bank (Burlingame, Calif., USA).

Fmoc-Amino Acid Active Esters were obtained from Cambridge Research Biochemicals (Cambridge, England); Epitope Scanning Kit is from Mimotopes (Australia); dimethylformamide "DMF", methanol "MeOH", piperidine, acetic anhydride, trifluoroacetic acid "TFA", phenol, phosphate buffered saline "PBS", dichloromethane "DCM", triethylamine, diisopropylethylamine, ethandithiol "EDT", hydroxy benzotriazole "HoBt", mercaptoethanol, bovine serum albumin "BSA", nitro blue tetrozolium chloride "NBT", 5-bromo-4-chloro-3-indolyl phosphate "BCIP", p-cresol, polyoxyethylene (20) sorbitan monolaurate "Tween 20™", 1,3-Dicyclohexylcarbodiimide "DCC", sodium dodecyl sulfate "SDS", 1-ethyl-3-(3-dimethylaminopropyl) carbodiimide hydrochloride "EDC", and ovalbumin were obtained from Aldrich (Milwaukee, Wis.); amino acids were obtained from Peninsula Lab. Inc. (Belmont, Calif.); hydroxy flouroacetic acid "HF" was obtained from (Soxal, Singapore).

All reagents used in the automated peptide synthesis method were obtained from Applied Biosystems (Foster City, Calif.).

EXAMPLE 1

Peptide Synthesis of NS1 Spanning Nonamers

Overlapping nonapeptides are synthesized on polyethylene pins using the commercially available Epitope Scanning Kit (Mimitopes, Australia). The synthesis procedure has been described previously (Geysen et al. 1984, 1987).

Peptides which are nine amino acids in length and which overlap by six residues are synthesized so as to span the C-terminal 351 amino acids of the 352 amino acid NS1 polypeptide, using active esters (pentafluoropheyl derivatives) of Fmoc-L-amino acids. The synthesis reactions are carried out on polyethylene pins attached to polypropylene blocks supplied by the manufacturer of the kit (Mimotopes, Australia). The blocks are constructed in order to perform synthesis reactions in the wells of 96-well microtitre dishes. All washing steps are carried out in baths containing enough wash solution to completely submerge the pins. The synthesis reactions are carried out in wells filled with amino acid solutions. The amino acid sequence of each peptide constructed is listed in Table 7, below.

Blocks of pins are deprotected using 20% piperidine in DMF for 30 minutes at room temperature and subsequently washed with DMF and MeOH before adding amino acids. The couplings of amino acids are carried out in DMF in the presence of the catalyst hydroxybenzotriazole (Hobt). Again, washes using DMF and MeOH are performed after coupling. These deprotection, washing, coupling and washing steps are repeated until all the amino acids coupled; i.e., until a nonapeptide is synthesized on each pin. The on-pin peptides are then subject to acetylation of terminal amino group using the following mixture: DMF: acetic anhydride-:triethylamine mixed 5:2:1 (v/v/v). The peptides undergo further a side chain deprotection and neutralization step using triflouroacetic acid, phenol and ethanedithiol mixed 95:2.5:2.5 (v/w/v), prior to epitope scanning assays.

TABLE 7

Nonamer Peptides for the Epitope Mapping Assay

| | | | | |
|---|---|---|---|---|
| 1) SGCVVSWKN | 24) ITPELNHIL | 47) TAECPNTNR | 70) TWKMEKASF | 93) DFCEGTTVV |
| 2) VVSWKNKEL | 25) ELNHILSEN | 48) CPNTNRAWN | 71) MEKASFIEV | 94) EGTTVVVTE |
| 3) WKNKELKCG | 26) HILSENEVK | 49) TNRAWNSLE | 72) ASFIEVKSC | 95) TVVVTEDCG |
| 4) KELKCGSGI | 27) SENEVKLTI | 50) AWNSLEVED | 73) IEVKSCHWP | 96) VTEDCGNRG |
| 5) KCGSGIFIT | 28) EVKLTIMTG | 51) SLEVEDYGF | 74) KSCHWPKSH | 97) DCGNRGPSL |
| 6) SGIFITDNV | 29) LTIMTGDIK | 52) VEDYGFGVF | 75) HWPKSHTLW | 98) NRGPSLRTT |
| 7) FITDNVHTW | 30) MTGDIKGIM | 53) YGFGVFTTN | 76) KSHTLWSNG | 99) PSLRTTTAS |
| 8) DNVHTWTEQ | 31) DIKGIMQAG | 54) GVFFTNIWL | 77) TLWSNGVLE | 100) RTTTASGKL |
| 9) HTWTEQYKF | 32) GIMQAGKRS | 55) TTNIWLKLR | 78) SNGVLESEM | 101) TASGKLITE |
| 10) TEQYKFQPE | 33) QAGKRSLRP | 56) IWLKLREKQ | 79) VLESEMIIP | 102) GKLITEWCC |
| 11) YKFQPESPS | 34) KRSLRPQPT | 57) KLREKQDVF | 80) SEMIIPKNF | 103) ITEWCCRSC |
| 12) QPESPSKLA | 35) LRPQPTELK | 58) EKQDVFCDS | 81) IIPKNFAGP | 104) WCCRSCTLP |
| 13) SPSKLASAI | 36) QPTELKYSW | 59) DVFCDSKLM | 82) KNFAGPVSQ | 105) RSCTLPPLR |
| 14) KLASAIQKA | 37) ELKYSWKTW | 60) CDSKLMSAA | 83) AGPVSQHNY | 106) TLPPLRYRG |
| 15) SAIQKAHEE | 38) YSWKTWGKA | 61) KLMSAAIKD | 84) VSQHNYRPG | 107) PLRYRGEDG |
| 16) QKAHEEGIC | 39) KTWGKAKML | 62) SAAIKDNRA | 85) HNYRPGYHT | 108) YRGEDGCWY |
| 17) HEEGICGIR | 40) GKAKMLSTE | 63) IKDNRAVHA | 86) RPGWHTQTA | 109) EDGCWYGME |
| 18) GICGIRSVT | 41) KMLSTESHN | 64) NRAVHADMG | 87) WHTQTAGPW | 110) CWYGMEIRP |
| 19) GIRSVTRLE | 42) STESHNQTF | 65) VHADMGYWI | 88) QTAGPWHLG | 111) GMEIRPLKE |
| 20) SVTRLENLM | 43) SHNQTFLID | 66) DMGYWIESA | 89) GPWHLGKLE | 112) IRPLKEKEE |
| 21) RLENLMWKQ | 44) QTFLIDGPE | 67) YWIESALND | 90) HLGKLEMDF | 113) LKEKEENLV |
| 22) NLMWKQITP | 45) LIDGPETAE | 68) ESALNDTWK | 91) KLEMDFDFC | 114) KEENLVNSL |
| 23) WKQITPELN | 46) GPETAECPN | 69) LNDTWKMEK | 92) MDFDFCEGT | 115) NLVNSLVTA |

EXAMPLE 2

Nonameric Peptide ELISA Assay

The on-pin peptides synthesized in Example 1 are screened for their antigenicities using the ELISA procedure accompanying the Epitope Scanning Kit (Mimotopes, Australia) but with slight modifications.

In 96-well microtitre plates, the pins with peptides permanently coupled to them are blocked with a super cocktail of ovalbumin (1%), BSA (1%) and Tween 20™ (0.1%) in 200 ul/well phosphate buffered saline (PBS) for an hour at 25° C. prior to immunoassay. Following the blocking step, the pins are incubated with a first serum sample from the group listed in Table 1. The serum samples are diluted 1/500 in super cocktail and each pin is incubated in 175 ul of the diluted serum overnight at 4° C. The pins are subsequently washed 4 times for 10 minutes each with PBS/Tween 20™. The pins are further incubated in 175 ul phosphatase labeled anti-human IgG diluted to 1:1,000 in super-cocktail for 60 minutes at room temperature with agitation. After washing again with PBS/Tween 20™, the pins are then incubated with 150 ul of the substrate solution (BCIP/NBT) for about 30 minutes in the dark until the substrate solution has produced visible color.

The pins with peptides permanently coupled to them are regenerated by sonication and the procedure above is repeated for each of the seven serum samples listed in Table 1.

The optical density of the reaction medium in each well is determined by a spectrophotometric plate-reader at 405/620 nm. The results are analyzed by a computer program supplied with the Epitope Scanning Kit as recommended by the manufacturer (Mimotopes, Australia). The results may be found in Table 2 above.

EXAMPLE 3

Synthesis of LPS122, LPS177 and LPS213

Based on the combined results of mapping, comparison and hydrophilicity profile, peptide LPS122 is synthesized manually using a MilliGen shaker (Model 403, Millipore, USA) using the solid phase peptide synthesis protocol "Schedule A" with modifications from Stewart and Young (1984), and peptides LPS177 and LPS213 (sequences listed in Table 3) are synthesized on an automated synthesizer (Applied Biosystems Inc., USA). A solid phase peptide synthesis method developed by Merrifield (1963) was adapted (Users Manual, Applied Biosystems, version 1.2:/8/15/89, p14–24) and is used in production of the peptides.

A. Manual Synthesis of LPS122

A preloaded resin (Boc-Glu($OB_2I$) -O-Resin) is used as the solid support for peptide synthesis. Boc-amino acids are used as raw materials to grow the peptide chains. The alpha-amino and side chain functionalities of these amino acids have been protected to prevent unwanted reactions.

The following steps are done on a Milligen shaker, rocking lightly such that the resin became fully suspended in each reaction and wash reagent. First, 860 milligrams of resin in a 2×10 cm reaction vessel is washed with 15 ml dichloromethane (DCM) 3 times for 5 minutes each. Second, DCM is removed and the resin washed with 15 ml trifluoroacetic acid (TFA)-DCM-Indole (1:3 with 1 mg/ml indole) for 90 seconds and removed. Then 15 ml of the TFA-DCM-Indole mixture is added again and incubated for 30 minutes to remove the Boc group in the third step. Fourth, the resin is washed 6 times with 15 ml DCM for 9 minutes each. Fifth, the DCM is removed and neutralization is accomplished by incubating the resin in 15 ml TEA-DCM 1:9 (v/v) for 90 seconds twice. Sixth, the resin is again washed 6 times in 15 ml DCM for 9 minutes each. Seventh, the Boc-amino acid is added to the resin in a 10 ml volume (3.0 mmoL) for 90 seconds. Eighth, 1.5 mmol of DCC in 0.25 ml of DCM is then added and the coupling reaction is allowed to proceed for 2 hours. Steps 4 through 8 are repeated for each amino acid and the resin is finally washed 3 times in 15 ml DCM for 5 minutes each.

Peptides are finally released from the resin subject to the following cleavage conditions. 20 ml of HF is mixed with 1 ml p-cresol, 0.2 ml EDT and 40 mg Methionine to form the cleavage mixture. The peptide-resin (1.7 grams) is allowed to react in the mixture for one hour at 0° C. The cleavage mixture is removed and the resin is washed with 2 ml TFA. The peptides are separated from the resin by filtration and the peptides precipitated with ether. The precipitated peptides are washed three times in ether and dried. The dry pellet had a weight of 780 mg.

B. Automated synthesis of LPS177 and LPS213

Automated peptide synthesis is performed using the Applied Biosystems Model 431A (Foster City, Calif., USA). HMP (p-hydroxymethylphenoxymethylpolystyrene) resin is used as the solid support to which the first amino acid is covalently bound. Fmoc-chemistry is used for this synthesis.

In the activation step, 1.0 mmoL dry, protected amino acid in a cartridge is dissolved with a solution of NMP and 1 ml of 1M HoBt in NMP. To this solution 1 ml of 1M DCC in NMP is added. After approximately 40 to 50 minutes of activation, the HOBt active ester is transferred to the reaction vessel while the DCU precipitate remained in the activator vessel.

In the coupling step, the Fmoc amino acid is reacted with the amino-terminal of the growing peptide chain to form a peptide bond. The standard scale cycles on the Model 431A are used in which four equivalents of the activated amino acid are added to each one equivalent of the growing peptide chain.

When coupling is complete, the resin is washed with NMP. Deprotection and coupling steps are repeated with each subsequent amino acid until the chain assembly has been completed.

The standard scale cycle uses 1 mmol Fmoc-amino acid, HOBt-active ester with 0.25 mmol resin. Deprotection is achieved by adding 20% piperidine in NMP for 21 minutes. Coupling is accomplished by adding the Fmoc amino acid HOBt ester in NMP and reacting it for 71 minutes.

Peptides are cleaved from the resin by placing the peptide-resin in a round-bottom flask that contains a micro stir bar. The flask is cooled on ice for 5 minutes. A cleavage mixture containing: 0.75 g crystalline phenol, 0.25 ml EDT, 0.5 ml thioanisole, 0.5 ml $H_2O$, and 10 ml TFA, is cooled and added to the peptide resin to give a total reaction volume of 10 ml per 0.1–1.5 g of peptide resin. The mixture is allowed to warm to room temperature and to react for 2–3 hours. The peptides are again separated from the resin by filtration and subsequent precipitation with ether. Peptides are extracted with ether three times before being dried.

The purity of these peptides are analyzed by reverse-phase high-performance liquid chromatography using a Delta pak C18-100A column (3.9 mm×30 cm) on a Waters HPLC system coupled with a Data Module 745. The compositions of peptides are verified by amino acid analysis using a Waters Pico-tag system (Millipore-Waters, Cambridge, Mass., USA).

The peptides are released from the resin as was peptide LPS122 above. 890 mg of LPS177 and 760 mg of LPS213 was obtained.

EXAMPLE 4

Coupling Peptides to BSA

Peptides are coupled onto BSA using carbodiimidies (Bauminger and Wilchek, 1980). 5 mg of each peptide is dissolved in 2 ml $H_2O$. The peptide is activated by addition of 50 mg 1-ethyl-3-(3-dimethylaminopropyl) carbodiimide hydrochloride (EDC) to the dissolved peptide and the pH is adjusted with NaOH/acetic acid to pH 5.0. BSA is dissolved in $H_2O$ and diluted to a 20 mg/ml solution. 1 ml of the BSA solution is added to the dissolved peptide such that a final molar ratio of approximately 4 mole of peptide to 1 mole of BSA results. The mixture is left at room temperature for four hours. 0.33 ml 1M sodium acetate (pH 4.2) is added to the peptide-BSA solution and left for an additional hour to stop the reaction. The peptide-BSA conjugates are dialyzed against PBS overnight.

EXAMPLE 5

Immunoassay of Larger Peptides

Peptides LPS122, LPS177, and LPS213 and their conjugated forms are tested for immunoreactivity toward human serum samples taken from patients infected with dengue virus. Peptides are immobilized on 0.2 um nitrocellulose membranes with the aid of the Immunetics Miniblotter system (Immunetics, Cambridge, Mass., USA) following the manufacturers instructions. The membranes are wetted in PBS for 5 minutes prior to the slotting of approximately 1 ul of synthetic peptides (coupled peptides 12–74 ug/ml; uncoupled peptides 200–1600 ug/ml in carbonate buffer, pH 9.2) per mm width of membrane. The membranes are then blocked with 5% skim milk (powder) in PBS for 45 minutes to reduce nonspecific binding and washed in PBS containing 0.05% Tween 20™ for 30 minutes. The slotted membranes are dried at 37° C. in an incubator for 2 hours.

The membrane strips are cut to approximately 3 mm in width and incubated with a 1:50 dilution of each patient's serum in a PBS-5% skim milk (powder) solution for 2 hours. The strips are washed with PBS/0.05% "Tween 20™" (Sigma) and then reacted with anti-human IgG conjugated with alkaline phosphatase for an additional one hour. After further washes, bound antibody is detected by incubation for 15 minutes with 2 ml of a substrate solution containing 5-bromo-4-chloro-3-indolyl-phosphate (BCIP) and nitroblue tetrazolium (NBT) (1:1) in 0.1M Tris buffer.

Although the invention has been described with reference to particular embodiments, methods, construction and use, it will be apparent to those skilled in the art that various changes and modifications can be made without departing from the invention.

It is claimed:

1. A peptide antigen, consisting of a peptide fragment derived from dengue virus serotype NS1 protein as shown in FIG. 2, characterized by:

(i) containing less than about 30 amino acid residues, and (ii) containing an epitope formed by the peptide sequence presented as SEQ ID NO: 9.

2. The peptide antigen of claim 1, wherein said peptide fragment contains the amino acid sequence presented as SEQ ID NO: 9.

3. The peptide antigen of claim 1, wherein said peptide fragment contains the amino acid sequence presented as SEQ ID NO: 1.

4. The peptide antigen of claim 1, wherein said peptide fragment contains the amino acid sequence presented as SEQ ID NO: 2.

5. A method of detecting dengue virus infection in a test individual, comprising providing at least one antigen which is selected from the claim 1, reacting serum from the test individual with such antigen, and examining said antigen for the presence of bound antibody.

6. The method of claim 5, wherein the antigen provided is attached to a solid support, said reacting includes contacting such serum with the support and said examining includes reacting the support and bound antibody with a reporter-labeled anti-human antibody.

7. A kit for ascertaining the presence of antibodies to dengue virus, comprising a solid support with at least one surface-bound recombinant peptide antigen selected from the group of peptides of claim 1.

* * * * *